United States Patent [19]

Dienes et al.

[11] 4,279,781
[45] Jul. 21, 1981

[54] CATALYST FOR THE SYNTHESIS OF METHANOL

[75] Inventors: Edward K. Dienes; Ray L. Coleman; Arthur L. Hausberger, all of Louisville, Ky.

[73] Assignee: United Catalysts Inc., Louisville, Ky.

[21] Appl. No.: 82,790

[22] Filed: Oct. 9, 1979

[51] Int. Cl.³ .................. B01J 21/04; B01J 23/06; B01J 23/72
[52] U.S. Cl. ................... 252/463; 252/475; 518/713
[58] Field of Search ............... 252/463, 475; 260/449.5

[56] References Cited

U.S. PATENT DOCUMENTS

| 2,061,470 | 11/1936 | Larson | 252/471 X |
| 3,326,956 | 6/1967 | Davies et al. | 252/468 X |
| 3,790,505 | 2/1974 | Casey et al. | 252/475 X |
| 3,840,478 | 10/1974 | Uda et al. | 252/468 |

FOREIGN PATENT DOCUMENTS 1159035 7/1969 United Kingdom ............... 260/449.5

*Primary Examiner*—W. J. Shine
*Attorney, Agent, or Firm*—William R. Price

[57] ABSTRACT

A methanol synthesis catalyst which comprises a major portion by weight of the oxides of copper and zinc and a minor portion by weight of a thermal stabilizing metal oxide is useful for the synthesis of methanol from the oxides of carbon and hydrogen at relatively low temperatures. The catalyst is characterized in that the ratio of copper oxide to zinc oxide, each expressed as a metal by weight, is in the range of from 2:1 to 3.5:1 and by the intimate association with each other of copper and zinc oxides and with said thermal stabilizing oxide. Further, the catalyst is characterized in that the amount of iron oxides, as an impurity, is less than 150 parts per million.

11 Claims, 4 Drawing Figures

1

CATALYST FOR THE SYNTHESIS OF METHANOL

BACKGROUND OF THE INVENTION

This invention relates to the production of methanol at relatively low temperatures and particularly to catalysts which are active for the production of methanol. On an industrial scale, methanol is generally prepared by the reaction of oxides of carbon with hydrogen. Generally, the prior art practice has been to react carbon monoxide or carbon dioxide with hydrogen using copper oxide and zinc oxide catalysts at temperatures in the range of 570° F. to 750° F. Because of equilibrium values, when the reaction of carbon dioxide and hydrogen is conducted at temperatures of 570° F. to 750° F., it is necessary to carry out this reaction at high pressures in order to obtain suitable yields. However, at these high temperatures and high pressures, the formation of higher molecular weight oxygenated hydrocarbons appear to occur. In fact, with a zinc oxide, chromium oxide catalyst, it is essentially impossible to obtain highpurity methanol at temperatures above 735° F. However, if the methanol synthesis reaction is carried out at lower temperatures, i.e., 400° F. to 560° F., there is a resulting approach to more favorable equilibrium conditions. Thus, it is highly desirable to provide a catalyst active for the synthesis of methanol in the lower temperature range.

DESCRIPTION OF THE PRIOR ART

Various catalyst containing the oxides of copper and zinc and containing additionally a thermal stabilizing metal oxide have been known for many years. As early as 1933, Dodge, in U.S. Pat. No. 1,908,696, disclosed a zinc oxide, copper oxide catalyst obtained by co-precipitation with sodium carbonate from a solution of their nitrates. Dodge disclosed a desired ratio of zinc to copper of 4:1 but stated that the zinc concentration could be reduced to a concentration of 2:1. The catalyst was calcined at a temperature of about 212° F. to 842° F. Larson, in 1936, disclosed a catalyst comprising a mixture of copper and zinc oxides in which the concentration of copper oxide exceeded the concentration of zinc oxide.

Tarhan, in U.S. Pat. No. 3,689,575, disclosed a process for the production of methanol utilizing catalyst consisting of the pre-reduced, mixed oxides of copper and zinc, copper and chromium, and copper, zinc and chromium in specified proportions.

Gallagher and Kidd, in British Pat. No. 1,159,035, disclosed methanol synthesis catalyst for use in the production of methanol with an atomic ratio of copper to zinc ranging from 1:2 to 3.8:1. Gallagher and Kidd also disclosed, in a preferred method of preparation of said catalyst, the co-precipitation of insoluble salts from a solution of metal nitrates utilizing sodium carbonate as the precipitant with a final pH of about 7.1. Thereafter, the slurry was filtered, washed and dried and calcined at about 572° F.

Casey, et. al., in U.S. Pat. No. 3,790,505, disclosed a low temperature methanol synthesis catalyst, prepared from oxides of copper and zinc obtained through the decomposition of ammine carbonates resulting from heat decomposition of copper and zinc ammine carbonates. These oxides were then mixed with aluminum oxide by high-speed shearing techniques to form a desired catalyst composition.

Stiles, in U.S. Pat. No. 4,111,847, taught the method of preparing a copper oxide, zinc oxide catalyst by co-precipitating zinc and copper carbonates from an aqueous solution of metal nitrates utilizing ammonium carbonate or bicarbonate as the precipitant and by utilizing nitrate solutions extremely low in sodium and sulfate ions.

SUMMARY OF THE INVENTION

According to this invention, a particularly active low temperature methanol synthesis catalyst comprises copper and zinc oxide in a ratio, expressed as metal by weight, of 2:1 to 3.5:1. The catalyst includes, preferably, a thermal stabilizing metal oxide such as aluminum oxide in minor proportions and is prepared by co-precipitation of all three constituents from a single solution of soluble zinc, copper and aluminum salts, say the nitrates, or by the decomposition of copper amine carbonates and zinc ammine carbonates onto a metal, thermally stabilizing metal oxide in the hydrated state, or as a gel. It is found that, if the catalyst is to be effective, it must have a relatively high surface area in excess, preferably, of 70 square meters per gram. The surface area appears to decrease with an increase in the calcination temperature so that the calcination temperature should not exceed under any circumstances, 600° F., and preferably is in the range of from 500° F. to 550° F. Nevertheless, the surface area is not wholly dependent upon the calcination temperature since other factors apparently affect the surface area of the catalyst. It has been found, however, that even minute quantities of iron oxide have an extremely deleterious effect upon the catalyst and that the concentration of iron oxide, expressed as a metal by weight should be less than 150 parts per million.

DETAILED DESCRIPTION OF THE INVENTION

Figure 1:
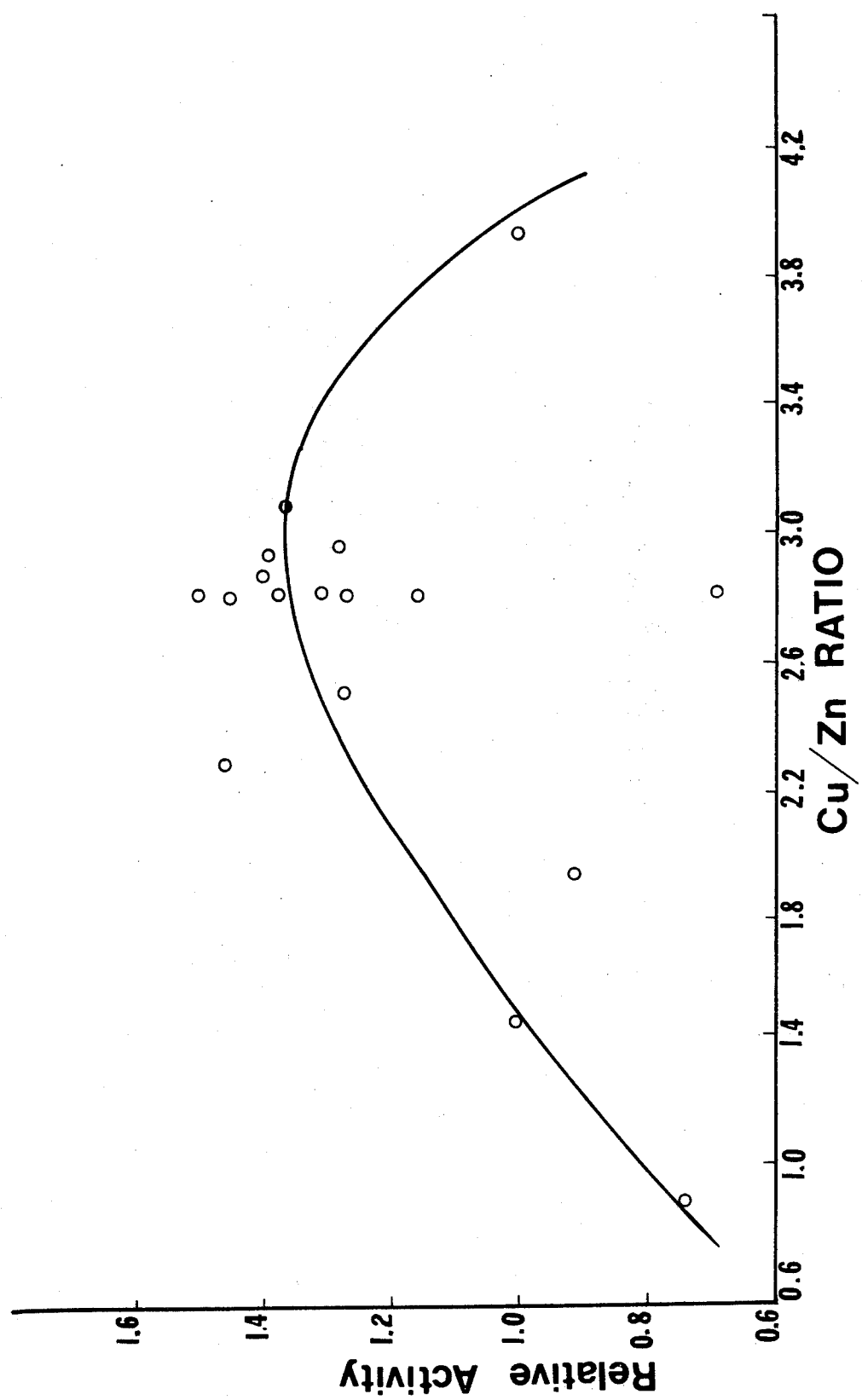
FIG. 1 is a plot of Relative Activity versus the Copper/Zinc Ratio for various catalysts in tests for the synthesis of methanol under identical conditions and utilizing the catalyst of Example 1B as the control.

The novel copper oxide-zinc oxide catalyst of this invention has a ratio of copper to zinc, expressed as the metal by weight, in the range of from 2:1 to 3.5:1. The catalyst contains thermally stabilizing metal oxides such as aluminum, zirconium, titanium, chromia, manganese, or magnesia. Preferably, aluminum oxide is used as the thermal stabilizing metal oxide in a concentration of about 10 percent by weight. Further, the concentration of copper oxide, expressed as a metal, should fall within the range of about 50 to 70 percent by weight and the concentration of zinc oxide, expressed as a metal, should be present in a concentration of 40 to 20 percent of weight. It is essential that the various metal oxides be in intimate association with each other. A preferred method of effecting this intimate association is by co-precipitation of all constituents from a common solution of their soluble metal salts, say, for example, the nitrates, to produce insoluble salts in intimate association as the precipitate. We have found that there is an optimum final pH of precipitation in the range of from 6.5 to 7.5 and preferably at about 7±0.1. Another method of intimately associating the oxides with each other is the simultaneous decomposition of ammine complexes, as for example, soluble copper and zinc tetra-ammine carbonates or soluble copper and zinc di- or tri-ammine carbonates. A mixture of these ammine complexes is heated for a period of time sufficient, and at a sufficiently high temperature, in the range of 160° F. to 210° F., to liberate ammonia and unreacted carbon dioxide and thereby form the water-insoluble basic carbonates. These hydroxycarbonates are precipitated, according to this invention, in the presence of or onto a hydrated alumina. The hydrated alumina can be simply gamma alumina with one water of hydration or can be an aluminum hydroxide precipitated from a solution of the nitrate salt. In any event, we have found that catalysts prepared in this method are quite satisfactory and for one reason or another appear to withstand calcination at a slightly higher temperature than the co-precipitated materials without affecting activity. The surface area, however, is quite important and in a preferred embodiment should be in excess of 70 $m^2/gm$ as measured by nitrogen adsorption. This factor is believed to be a function of the intimate association of copper oxide and zinc oxide and the crystallite size of the constituents.

Another important feature of this catalyst is the effect of minute quantities of iron oxide as an impurity. We have found, for example, that there is a sharp deleterious effect upon the activity of the catalyst if the iron oxide concentration is in excess of 150 parts per million. This appears to be true even if the copper to zinc ratio falls within the desired range, the precipitation is done at the desired end point, the surface area of the catalyst is above 70 $m^2/gm$ and all of the other factors are present. Nevertheless, the presence of even a minor amount of iron oxide apparently affects the activity of the catalyst appreciably and this constituent therefore is to be strenuously avoided.

As previously indicated, the catalyst thus prepared is particularly useful for the production of high-purity methanol. Nevertheless, it can be utilized at temperatures of from 450° F. to 750° F. and pressures of 300 to 1500 PSIG or, if desired, at even higher pressures of 1500 to 6000 PSIG. However, it is to be recognized that a major advantage of the catalyst is that it can operate at lower temperatures and pressures.

EXAMPLE 1

A 25-pound batch of catalyst is prepared as follows: A 6 percent solution of copper ammine carbonate, $Cu(NH_3)_6 \cdot CO_3$, was mixed with a 6 percent solution of zinc ammine carbonate, $Zn(NH_3)_6 \cdot CO_3$, so that the mixed copper-zinc solution contains 9.42 pounds of zinc, expressed as the metal, and 8.61 pounds of copper, expressed as the metal. This copper-zinc ammine carbonate complex was then mixed with 2.94 pounds of hydrated aluminum oxide, $Al_2O_3 \cdot H_2O$. The mixture was then heated on a hot plate until the copper and zinc ammine carbonates were decomposed to form basic zinc carbonates, i.e., copper-zinc hydroxycarbonate. The resulting slurry was then filtered and the filter cake was calcined for four hours at 600° F. The resulting oxide-carbonate mixture was then mixed with graphite and formed into 3/16 by 3/16 inch tablets. The resulting catalyst had a copper to zinc ratio of 0.92:1.

EXAMPLE 1-B

A 25-pound batch of catalyst was prepared identically to the preparation of Example A, except that the amounts of copper and zinc in the ammine complexes were varied so as to produce a copper to zinc ratio, expressed as the metal by weight, of 1.49:1.

EXAMPLE 1-C

Another 25-pound batch of catalyst was prepared in an identical method to Examples 1 and 1-B above, except that the amounts of copper and zinc in the copper ammine carbonate complexes were varied to produce a copper to zinc ratio, expressed as a metal by weight, of 2.52:1.

EXAMPLE 2-D

Another batch of catalyst was prepared by co-precipitation from a nitrate solution of insoluble copper, zinc and aluminum carbonates, utilizing sodium carbonate ($Na_2CO_3$) as the precipitating medium. In this example, a solution of the metal mitrates, containing 6.13 pounds of zinc expressed as the metal, 11.88 pounds of copper, expressed as the metal and 1.32 pounds of aluminum, expressed as the metal, was mixed with soda ash solution on a continuous basis. The solutions were put through a precipitator at 20 minutes retention and a final pH of 7.1. The resulting precipitation of basic carbonates was filtered from the solution, dried and calcined at 575° F. This catalyst contained a copper to zinc ratio, expressed as the metal by weight, of 1.95:1.

EXAMPLE 2-E

Another 25-pound batch of catalyst was prepared in the same manner as that of Example 2-D except that the amounts of copper and zinc in the nitrate solutions were varied so as to produce a copper to zinc ratio of 2.84:1.

EXAMPLE 2-F

Another 25-pound batch of catalyst was prepared by the identical method of Examples 2-D and 2-E, except that the copper and zinc concentrations of the nitrate solutions were varied so as to produce a copper to zinc ratio, expressed as the metal by weight, of 2.96:1.

EXAMPLE 2-G

Another 25-pound batch of catalyst was prepared by the identical method of Examples 2-D, 2-E and 2-F, except that the concentration of the copper and zinc compounds, expressed as the metal, in the nitrate solution, was varied so as to produce a copper to zinc ratio, expressed as the metal by weight, of 3.95:1.

EXAMPLE 2-H

Another 25-pound batch of catalysts was prepared according to procedures of the previous Examples 2 through G, except that the copper and zinc concentrations of the nitrate solution were varied so as to produce a finished catalyst having a copper to zinc ratio of 2.98:1. Additionally, the pH of the precipitating solution was raised to 7.5 and the calcination temperature lowered to 550° F.

EXAMPLE 2-I

Another 25-pound batch of catalyst was prepared under the identical conditions of Examples 2-D through H except that the copper and zinc concentrations of the nitrate solution were varied to produce in the finished catalyst, a copper to zinc ratio, expressed as the metal by weight, of 2.30:1. In this case, the final pH was 7.1 and the calcination temperature was at 550° F.

EXAMPLE 2-J

Again, another 25-pound batch of catalyst was prepared according to the general procedure set forth in Examples 2-D through I, except that the concentrations of the copper and zinc in the nitrate solution were varied so as to produce a copper to zinc ratio, expressed as the metal by weight, in the finished catalyst, of 2.83:1. The pH of the final solution in this example was 6.5 and the calcination temperature of the precipitate was 550° F.

EXAMPLE 2-F-1

Another 25-pound batch of catalyst was prepared by precipitation from the nitrate solution according to the methods previously set forth in Examples 2-D through J, except that the concentrations of copper and zinc in the nitrate solutions were varied so as to produce a copper to zinc ratio in the finished catalyst, expressed as the metal by weight, of 2.83:1. The final pH of the precipitation was 7.1 and the calcination temperature was raised in this example to 600° F.

EXAMPLE 2-F-2

Again, another 25-pound batch of catalyst was prepared according to the general methods set forth in Examples 2-D through 2-F-1, and the copper to zinc ratio was maintained at 2.83:1 but the calcination temperature was lowered to 575° F.

EXAMPLE 2-F-3

Another 25-pound batch of catalyst was prepared by the co-precipitation of the metal carbonates from their copper and zinc nitrate solutions so as to produce a copper to zinc ratio in the finished catalyst, expressed as the metal by weight, of 2.83:1. The final pH for the precipitation was 7.1. The catalyst was calcined in this example at 550° F.

EXAMPLE 2-I-1

Another 25-pound bath of catalyst was made by co-precipitation from a solution of metal nitrates so as to produce a finished catalyst having a copper to zinc ratio, expressed as the metal by weight, of 2.83:1. The calcination temperature was 600° F.

EXAMPLE 2-I-2

Another batch of catalyst was made by co-precipitation from a nitrate solution having a proper concentration of copper to zinc so as to produce a copper to zinc ratio of 2.83:1. Sodium carbonate was used as the precipitant with a final pH of 7.1. The calcination temperature of the dried precipitate was 550° F.

EXAMPLE 2-I-3

Another 25-pound batch of catalyst was made by co-precipitation from a nitrate solution containing copper and zinc in the proper concentrations to produce a copper to zinc ratio, expressed as the metal by weight, of 2.83:1, utilizing sodium carbonate as the precipitant and maintaining the final pH of the precipitation at 7.1. The calcination temperature of the dried precipitate was 530° F.

TEST CONDITIONS

For the sake of uniformity, all tests of catalysts prepared in Examples 1 and 2 were carried out under the same conditions. All the runs were carried out at a temperature of 450° F., a pressure of 750 PSIG and a space velocity of 13,000 volumes of gas/volumes catalyst/hour. The gas composition was as follows:

| Constituent | Percentage |
|---|---|
| CO | 3.7 |
| $CO_2$ | 2.3 |
| Inerts | 11 |
| $CH_4 + N_2$ | |
| $H_2$ | 83.0 |

Catalyst 1-B was taken as the control sample. Therefore, its relative activity was 1. Table 1 is a tabulation showing the copper oxide to zinc oxide ratio (expressed as the metal) and the effect of this ratio upon the yield and upon the relative activity of the catalyst. This is plotted in FIG. 1 as Relative Activity versus Cu:Zn Ratio.

TABLE I

| Example | Copper:Zinc Ratio (Expressed as metal) | Calcination Temp. °F. | Surface Activity $m^2$/gm BET | pH | Yield cc/cc/hr *** | Relative Activity |
|---|---|---|---|---|---|---|
| 1A | .92:1 | 600 | 47.0 | | 0.274 | 0.753 |
| 1B (Control) | 1.49:1 | 600 | 62.1 | | 0.364 | 1.000 |
| 1C | 2.52:1 | 600 | 60.3 | | .460 | 1.266 |
| 2D | 1.95:1 | 575 | 62.0 | 7.1 | .331 | .908 |
| 2E | 2.84:1 | 575 | 80.7 | 7.1 | 0.507 | 1.394 |
| 2F | 2.96:1 | 575 | 86.2 | 7.1 | 0.500 | 1.373 |
| 2G | 3.95:1 | 575 | 63.2 | 7.1 | 0.364 | .999 |

***cc methanol/cc catalyst/hour

Note, for example, that in Table I, catalyst 1C, prepared by the decomposition of copper-zinc ammine carbonates onto hydrated alumina, had a relative activity of 1.26 whereas the same catalyst 1A, prepared identically except for the copper:zinc ratio, had a relative activity of 0.753. Note also that the surface area of the catalyst 1C was higher than the surface area of catalyst 1A, i.e., 60.3$m^2$/gm, as compared to 47$m^2$/gm. This phenomenon was true even though the calcination temperature of each of the samples was identical, i.e., 600° F. Further, catalysts 2E and 2F again show the unexpected effect of the copper:zinc ratio within the claimed range in increasing the yield and the relative activity. Note, for example, that catalyst 2D, having a copper to zinc ratio of 1.95:1, had a relative activity of 0.908, less than 1, whereas catalysts prepared within the claimed range had relative activities of 1.394 and 1.373 to 1, respectively. Please also note that even though the calcination temperature was identical for the Example 2 series, that the surface area of catalyst having a copper to zinc ratio, within the claimed range, was higher than that outside of the claimed range.

EFFECT OF FINAL pH DURING PRECIPITATION

Referring now to Table II, it will be seen that the final pH appears to have an effect upon the yield and relative activity of the catalyst.

TABLE II
EFFECT OF pH DURING PRECIPITATION

| Example | pH | Calcination Temp. °F. | Surface Area m²/gm BET | Yield cc/cc/hr | Relative Activity |
|---|---|---|---|---|---|
| 2H | 7.5 | 550 | 72 | 0.464 | 1.275 |
| 2I | 7.1 | 550 | 83 | 0.531 | 1.460 |
| 2J | 6.5 | 550 | 80 | 0.474 | 1.303 |

Note, for example, in Table II, that Example 2I, having a final pH of 7.1, was more active than the identical catalyst which was precipitated at a final pH of 7.5 or of the identical catalyst, Example 2J, precipitated at a final pH of 6.5.

the preferred range. The trend, however, appears to be absolutely clear that the lower the calcination temperature, the higher the relative activity.

It was felt, therefore, that all of the factors had been pretty well defined so as to produce catalysts of uniform activity at low temperatures. However, in a series of catalysts prepared under identical conditions (according to the procedure of Example 2-I-3 and of the same composition and Cu:Zn ratio), unexplained variations in relative activity appeared. Upon closer study, it was found that this series of catalysts prepared for pilot plant testing, under conditions more akin to plant preparation, rather than laboratory preparation, contained iron oxide impurities. These impurities were apparently introduced in the form of contaminants from scale in the tanks and from certain impurities in the water supply. Thus, it will be seen that concentrations of iron oxide, as low as 150 parts per million, had an appreciable deleterious effect upon the activity of the catalyst. These catalysts were run under different conditions than the previous catalysts. Nevertheless, it can be seen that essentially identical yields were obtained so long as the iron oxide concentration was less than 150 parts per million. However, at concentrations in excess of that figure, the yield dropped sharply.

Of course, it is possible to utilize extreme care in the selection of the chemicals so that the iron oxide impurities are not introduced at all. Thus, for example, in the

TABLE III
MASTER TABLE

| Example No. | Percentage by Weight CuO | Percentage by Weight ZnO | Percentage by Weight Al₂O₃ | Ratio of Cu:Zn* | Crystal Size CuO** | Method of Prep. | pH | Calc. Temp. | Surface Area | Yield cc/cc/hr | Relative Activity |
|---|---|---|---|---|---|---|---|---|---|---|---|
| 1A | 43.2 | 47.0 | 10.2 | .92:1 | 80 | Ammine | | 600 | 47.0 | .274 | .753 |
| 1B | 51.4 | 34.5 | 13.6 | 1.49:1 | 70 | Ammine | | 600 | 62.1 | .364 | 1.000 |
| 1C | 62.9 | 25.0 | 12.1 | 2.52:1 | 70 | Ammine | | 600 | 60.3 | .460 | 1.266 |
| 2D | 58.8 | 30.1 | 11.1 | 1.95:1 | 50 Nit. | Prec. | 7.1 | 575 | 62.0 | .331 | .908 |
| 2E | 64.1 | 22.5 | 13.4 | 2.84:1 | 65 Nit. | Prec. | 7.1 | 575 | 80.7 | .507 | 1.394 |
| 2F | 67.3 | 22.7 | 10.0 | 2.96:1 | 55 Nit. | Prec. | 7.1 | 575 | 86.2 | .500 | 1.373 |
| 2G | 71.9 | 18.2 | 9.9 | 3.95:1 | 55 Nit. | Prec. | 7.1 | 575 | 63.2 | .364 | .999 |
| 2H | 67.1 | 22.5 | 10.4 | 2.98:1 | 68 Nit. | Prec. | 7.5 | 550 | 72.0 | .464 | 1.275 |
| 2I | 65.7 | 28.6 | 11.0 | 2.30:1 | 50 Nit. | Prec. | 7.1 | 550 | 83.0 | .531 | 1.460 |
| 2J | 65.4 | 23.1 | 11.5 | 2.83:1 | 68 Nit. | Prec. | 6.5 | 550 | 80.0 | .474 | 1.303 |
| 2F₁ | 65.4 | 23.1 | 11.5 | 2.83:1 | 130 Nit. | Prec. | 7.1 | 600 | 34.5 | .249 | .685 |
| 2F₂ | 65.4 | 23.1 | 11.5 | 2.83:1 | 55 Nit. | Prec. | 7.1 | 575 | 55.3 | .421 | 1.157 |
| 2F₃ | 65.4 | 23.1 | 11.5 | 2.83:1 | 50 Nit. | Prec. | 7.1 | 550 | 86.2 | .500 | 1.373 |
| 2I₁ | 65.4 | 23.1 | 11.5 | 2.83:1 | 70 Nit. | Prec. | 7.1 | 600 | 72.9 | .459 | 1.262 |
| 2I₂ | 65.4 | 23.1 | 11.5 | 2.83:1 | 50 Nit. | Prec. | 7.1 | 550 | 83.0 | .531 | 1.460 |
| 2I₃ | 65.4 | 23.1 | 11.5 | 2.83:1 | 50 Nit. | Prec. | 7.1 | 530 | 78.0 | .542 | 1.488 |

Figure 2:
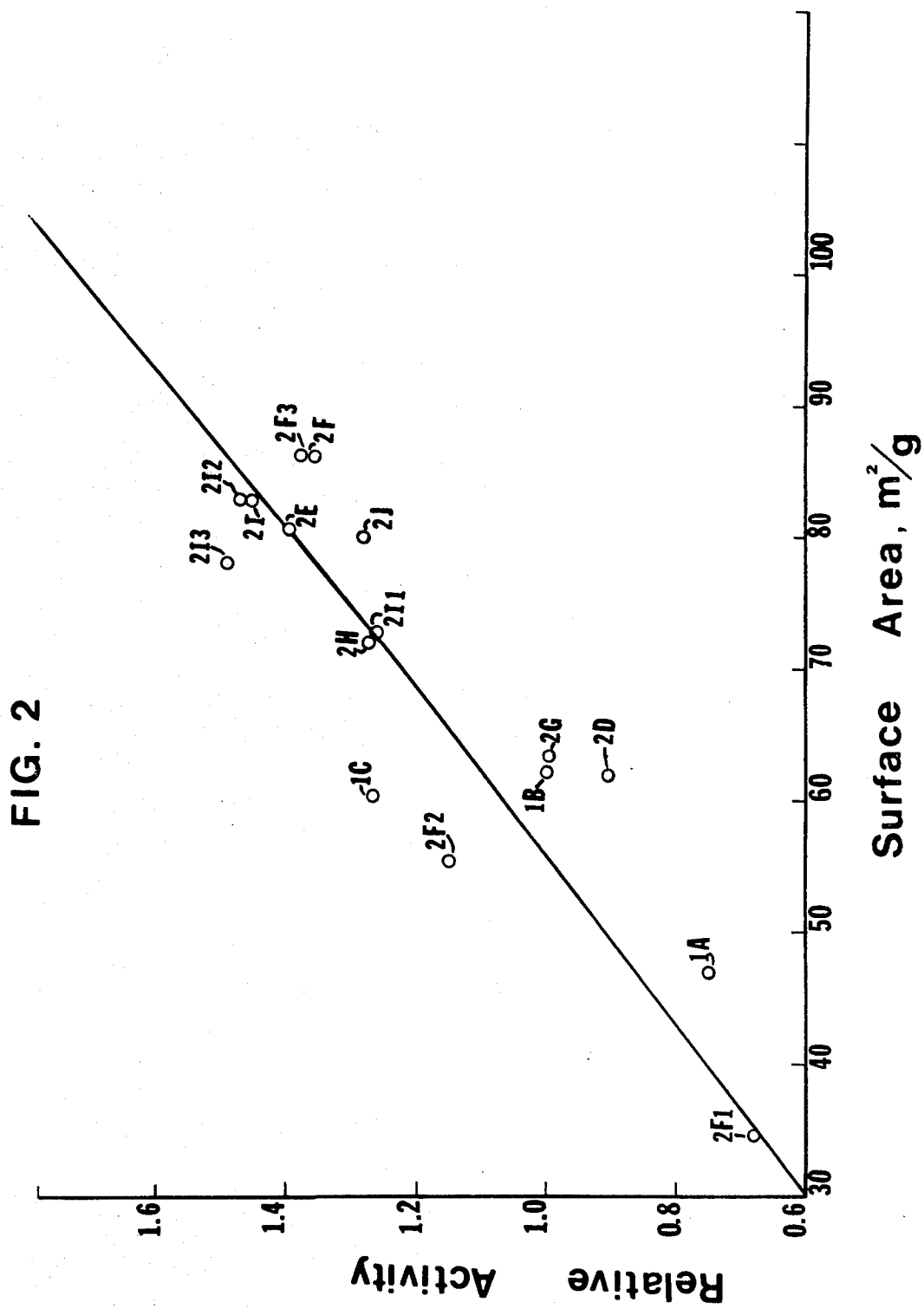
FIG. 2 is a plot of Relative Activity versus Surface Area of various catalysts tested under identical conditions for the synthesis of methanol.
Figure 3:
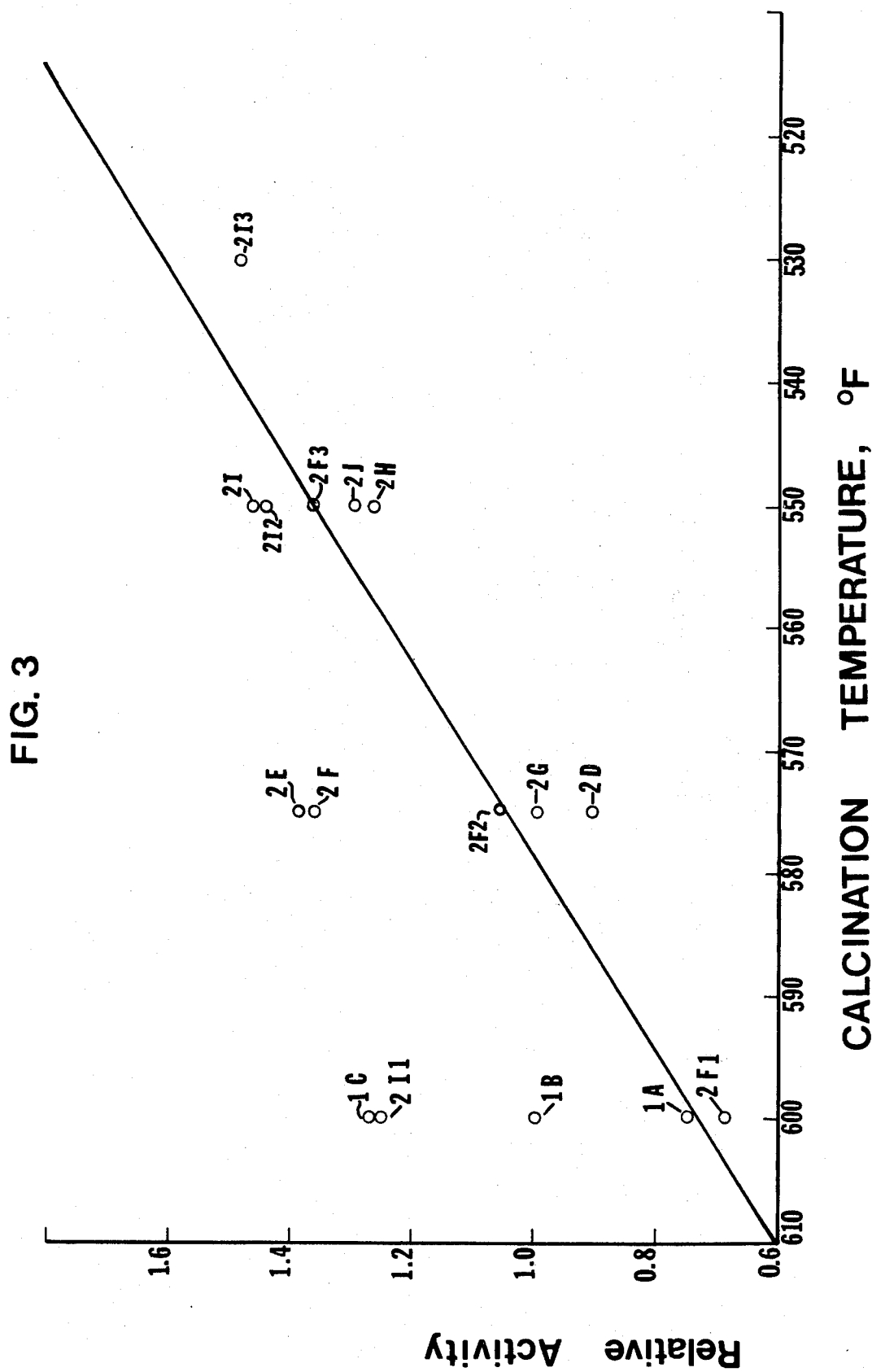
FIG. 3 is a plot of Relative Activity versus Calcination Temperature of various catalysts tested under identical conditions for the synthesis of methanol.
Figure 4:
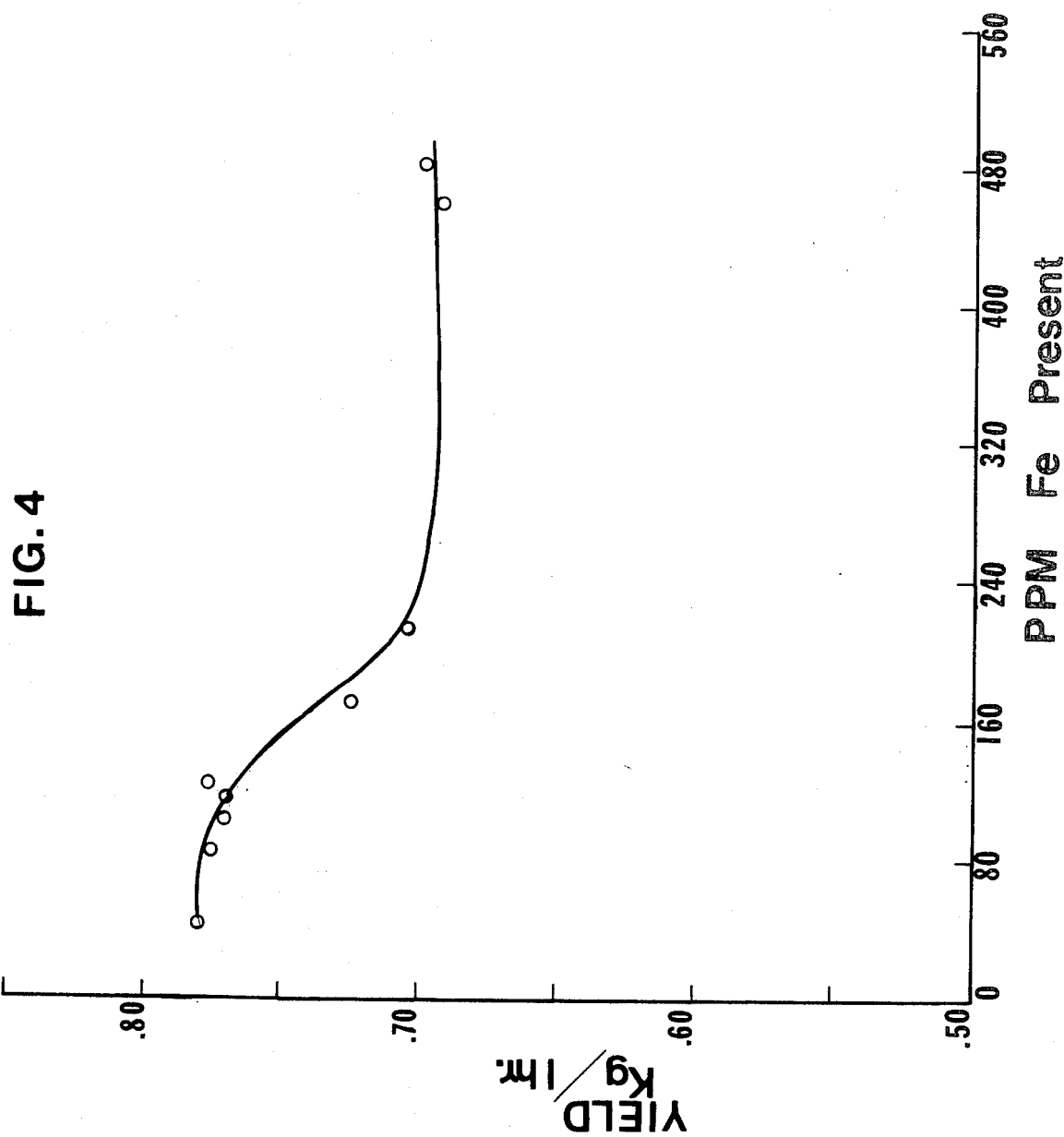
FIG. 4 is a plot of yield versus ppm/$Fe_2O_3$ of catalysts of identical composition which have been prepared and tested identically for the synthesis of methanol which demonstrates the extremely deleterious effect of minute amounts of iron oxide upon the yield.

*Percentage by weight of constituents, present as oxides but expressed as the metal by weight.
**Angstroms It has also been found, by reference to FIG. 2, in which the data selected from Table III, is plotted, that the relative activity of these catalysts appear to increase with the surface area. Thus, it can be seen, with one exception, i.e., catalyst 1C, that the catalysts having a surface area of 70m²/gm or more, are more active than catalysts with surface areas less than that amount. Again, as shown in FIG. 3, in which the calcination temperature of the various samples are plotted against relative activity, it will be seen that catalysts calcined at a temperature of 550° F. or less appear to have better activity than catalysts calcined at temperatures of above 550° F. It should be noted again that these points on the graph are taken from the Master Table III and are not identically-prepared catalysts. In other words, the other variables previously mentioned are present and this apparently accounts for the somewhat scattered effect of the relative activities of catalysts 2F2, 2G and 2D, versus catalysts 2E and 2F, which were calcined within production of the copper and zinc ammine carbonates, the iron oxide can be prevented from entering the basic compounds so that the undesired concentrations are not found in the finished catalyst.

Many modifications will occur to those skilled in the art from the detailed descriptions hereinabove given and such is meant to be exemplary in nature except so as to be commensurate in scope with the appended claims.

We claim:

1. A methanol synthesis catalyst precursor, which comprises:
   A. a major portion by weight of the oxides of copper and zinc,
   B. a minor portion by weight of a thermal stabilizing metal oxide in which:

1. the ratio of copper oxide to zinc oxide, each expressed as the metal by weight, is in the range of from 2:1 to 3.5:1, and
2. the oxides of copper and zinc are in intimate association with each other and with said thermal stabilizing metal oxide, and in which
C. the concentration of iron oxide impurity in the total catalyst precursor, expressed as the metal by weight, is less than 150 parts per million in which said impurity is introduced in preparing the catalyst precursor.

2. A methanol synthesis catalyst precursor, as defined in claim 1, in which the surface area of the total catalyst precursor is at least 70 square meters per gram.

3. A methanol synthesis catalyst precursor, as defined in claim 1, in which the thermal stabilizing metal oxide is aluminum oxide.

4. A methanol synthesis catalyst precursor, as defined in claim 1, in which the copper and zinc oxides are derived through the co-precipitation to insoluble salts from an aqueous solution of soluble salts and the subsequent conversion of said insoluble salts to their oxides.

5. A methanol synthesis catalyst precursor, as defined in claim 4, in which the thermal stabilizing metal oxide is incorporated into the catalyst by co-precipitation of an insoluble salt from said aqueous solution.

6. A methanol synthesis catalyst precursor, as defined in claim 1, in which the concentration of copper oxide, expressed as the metal, is in the range of from 50 to 70 percent by weight.

7. A methanol synthesis catalyst precursor, as defined in claim 1, in which zinc oxide, expressed as the metal, is present in a concentration of 40 to 20 percent by weight.

8. A methanol synthesis catalyst precursor, as defined in claim 1, in which the thermal stabilizing metal oxide is aluminum oxide in a concentration, expressed as the metal of about 10 percent by weight.

9. A methanol synthesis catalyst precursor, as defined in claim 1, in which the oxides of copper and zinc are derived by the decomposition of an ammine complex containing copper and zinc, to heat decomposible salts of copper and zinc followed by conversion of said salts to their oxides.

10. A methanol synthesis catalyst precursor, as defined in claim 9, in which the decomposition of said ammine complex is onto a hydrated thermal stabilizing metal oxide.

11. A methanol synthesis catalyst precursor, as defined in claim 10, in which said hydrated thermal stabilizing metal oxide is a hydrated gel.

* * * * *